(12) United States Patent
Hunt et al.

(10) Patent No.: US 9,557,263 B2
(45) Date of Patent: Jan. 31, 2017

(54) TERAHERTZ MATERIAL EVALUATION AND CHARACTERIZATION VIA MATERIAL DIFFERENCE FREQUENCY GENERATION

(71) Applicant: The Boeing Company, Huntington Beach, CA (US)

(72) Inventors: Jeffrey H. Hunt, Thousand Oaks, CA (US); John H. Belk, St. Louis, MO (US)

(73) Assignee: THE BOEING COMPANY, Chicago, IL (US)

(*) Notice: Subject to any disclaimer, the term of this patent is extended or adjusted under 35 U.S.C. 154(b) by 145 days.

(21) Appl. No.: 14/520,694

(22) Filed: Oct. 22, 2014

(65) Prior Publication Data

US 2016/0116400 A1    Apr. 28, 2016

(51) Int. Cl.
*G01N 21/35* (2014.01)
*G01N 21/3581* (2014.01)
*G01N 21/39* (2006.01)
*G01N 21/3586* (2014.01)

(52) U.S. Cl.
CPC ...... *G01N 21/3581* (2013.01); *G01N 21/3586* (2013.01); *G01N 21/39* (2013.01); *G01N 2201/06113* (2013.01)

(58) Field of Classification Search
CPC .................................................. G01N 21/3581
See application file for complete search history.

(56) References Cited

U.S. PATENT DOCUMENTS

| | | | |
|---|---|---|---|
| 6,388,799 B1 * | 5/2002 | Arnone | G01N 21/3581 359/326 |
| 7,304,305 B2 | 12/2007 | Hunt | |
| 8,736,838 B2 | 5/2014 | Herzinger | |
| 8,743,368 B2 | 6/2014 | Meyers et al. | |
| 2007/0090294 A1* | 4/2007 | Safai | G01N 21/3581 250/341.8 |
| 2014/0061474 A1* | 3/2014 | Kitamura | G01J 3/42 250/339.02 |
| 2016/0119557 A1* | 4/2016 | Hunt | H04N 5/332 348/131 |

OTHER PUBLICATIONS

Oda, "Uncooled Bolometer-type Terahertz Focal Plane Array and Camera for Real-Time Imaging," C.R. Physique, vol. 11, 2010, pp. 496-509.

* cited by examiner

*Primary Examiner* — Casey Bryant

(57) ABSTRACT

Methods, systems and apparatuses are disclosed for interrogating characteristics of a substrate material surface and sub-surface by evaluating Terahertz output signals generated by non-Terahertz, optical source inputs.

18 Claims, 4 Drawing Sheets

TERAHERTZ MATERIAL EVALUATION AND CHARACTERIZATION VIA MATERIAL DIFFERENCE FREQUENCY GENERATION

TECHNOLOGICAL FIELD

The present disclosure relates to monitoring material surfaces and sub-surfaces. More particularly the present disclosure relates to monitoring material surfaces using second-order nonlinear optics to achieve Terahertz level material evaluation and characterization without the use of a Terahertz input.

BACKGROUND

In non-linear optical, or wave mixing processes, outputs are produced at sum, difference or harmonic frequencies of the input(s). Second order non-linear optics, or three wave mixing involves combining two inputs to produce one output at one of the combined frequencies. The use of second order non-linear optical surface spectroscopy to examine physical properties of a material surface is known. However, practical constraints on such known methods have impeded progress on the material evaluation and characterization beneath the surface of a material under inspection.

The Terahertz (hereinafter "THz") range refers to electromagnetic waves with frequencies between 100 GHz and 10 THz, or wavelengths between 3 mm and 30 µm, existing in the radiation spectrum between the microwave and infrared region. Terahertz waves are known to pass through a variety of amorphous and opaque substances. In addition, many biomolecules, proteins, explosives or narcotics also feature characteristic absorption lines, so-called spectral "fingerprints", at frequencies between 0.3 and 3 THz. The two main advantages of THz radiation are thus the penetration of conventionally opaque materials on one hand, and a high chemical selectivity on the other hand. Terahertz imaging is therefore thought to be a non-destructive technique for interrogating dielectric (non-conducting) materials. The use of terahertz waves for non-destructive evaluation of materials enables inspection of multi-layered structures and can therefore identify abnormalities from foreign material inclusions (contamination), delamination, heat damage, etc.

The spectroscopic frequency band of a 0.1 to 10 THz is not easily accessible. Electronic sources like Gunn or Schottky diodes with subsequent frequency multipliers, provide high output levels (mW range), up to some 100 GHz, yet become inefficient in the sub-millimeter range. Direct optical sources, like quantum cascade lasers, are usually limited to frequencies greater than 5 THz, even when operated at cryogenic temperatures.

Optoelectronic THz generation is an expression for indirect methods, where near-infrared laser light illuminates a metal-semiconductor-metal structure, generating a photocurrent that becomes the source of a THz wave. Both pulsed and continuous-wave (CW) techniques have been realized, and both have their advantages and limitations. Pulsed THz radiation offers a higher bandwidth (typically from about 0.1 to about 10 THz) and permits very fast measurements (a spectrum can be acquired within milliseconds). On the other hand, the frequency resolution is limited to several GHz. Vice versa, a CW system features a somewhat lower bandwidth (typically from about 0.1 to about 2 THz) and requires longer measurement times (acquiring a spectrum takes several minutes), yet the frequency can be controlled with extreme precision (down to single MHz).

Composite materials such as fiberglass, Kevlar and carbon fiber are increasingly being used as structural components in aircraft because of their high strength to weight ratios, improved performance, reduced corrosion, etc., compared with other known structural materials. However, composites can be weakened by various defects and stress during their life cycle. Further, routine maintenance of composites requires complicated inspection and repair techniques.

Terahertz radiation offers a non-invasive, non-contract, non-ionizing method of assessing composite part condition. However, THz sources have generally been difficult to produce. While there has been recent development using quantum cascade lasers, such devices remain largely in the developmental stage, and are intrinsically low-power devices. This limits their application to selected industrial manufacturing environments that require ease of operation and speed of data acquisition. In addition, use of THz surface of a substrate surface using presently available technology would still lack the degree of surface specificity required for interrogating composite and other opaque surfaces.

The use of composite materials in modern manufacturing scenarios requires the existence of diagnostics that can reliably interrogate surface and subsurface composite characteristics. Such interrogation developments were not required for interrogating previous metallic-based manufacturing, since such systems were developed based on several centuries of metal manufacturing experience. While x-ray technologies were adequate to perform subsurface measurements with metal substrates, concerns regarding health and safety of personnel have properly precluded their use and adaptation in all but the most carefully controlled environments, such as medical facilities.

SUMMARY

According to one aspect, the present disclosure is directed to methods, systems and apparatuses for evaluating and characterizing substrate material surfaces and sub-surfaces in the THz regime by using a plurality of optical source input radiation (non-THz regime sources). According to another aspect, the optical sources undergo second order mixing, specifically difference frequency generation (DFG). The present methods, systems and apparatuses require only optical sources, but achieve the effect of using THz regime radiation. The optical sources of inherent interest exist in abundance, can be operated for long-duration with reduced maintenance, have a comparatively easy set-up, and can be easily inspected.

According to the methods, systems and apparatuses disclosed herein, it has now been demonstrated that THz regime investigation can be performed using only optical input sources that are in the optical regime. Desired effects in the THz regime are achieved via the use of non-linear optical interaction of optical source input beams at a material surface and/or sub-surface of a material being interrogated, by obtaining a difference frequency generation (DFG) between the two optical source inputs.

According to a further aspect, one or more properties of the substrate surface are measured based on the output beam received by the detector. A first optical input beam from a first optical source having a first frequency, for example, in the optical range of from about 10,000 $cm^{-1}$ to about 30,000 $cm^{-1}$, is directed onto a predetermined region of a substrate material surface. A second optical input beam from a second optical source having a second frequency different from the first source frequency, but, for example, between from about 10,000 cm$^{-1}$ to about 30,000 cm$^{-1}$ is directed onto a predetermined region of a substrate material surface. While the frequency of the first optical source is largely arbitrary (but within the stated range), the frequency of the second optical source differs from the first optical source by the amount of the desired THz frequency to be generated. The first and second input beams are mixed at or beneath the surface of the substrate material surface to provide an output beam having a THz frequency of from about 0.1 THz to about 100 THz. The output beam is received by a terahertz detector. One or more properties of the substrate material surface are measured based on the output beam received by the THz detector.

Therefore, according to one aspect, the present disclosure contemplates evaluating a substrate material surface comprising the steps of directing a first optical input beam from a first optical source having a first frequency onto a region of a substrate material surface; and directing a second optical input beam from a second optical source having a second frequency onto the region of the substrate material surface, with the first frequency of the first optical input beam differing from the second frequency of the second optical input beam. The first optical input beam and the second optical input beam are mixed at or beneath the substrate material surface to provide an output beam having a THz frequency. The output beam is directed to and received by a THz detector, and one or more properties of the substrate material surface are measured based on the output beam received by the detector.

According to aspect of the present disclosure, the disclosed methods, systems and apparatuses can measure changes in a substrate material surface and subsurface, or properties and characteristics of any substrate material. For example, such characteristics include, mechanical defects, surface roughness, molecular contamination by non-native species, surface molecular orientation, etc. and combinations thereof. According to an aspect of the present disclosure, while the achievable absolute sensitivity depends on the particular parameters of the optical sources, and detectors selected (such as, for example, signal-to-noise ratio, etc.), the resulting signal changes in an output beam from as little as a tenth of a molecular monolayer at the material substrate surface will be detected.

According to still further aspects, the difference between the first frequency of the first optical input beam and the second frequency of the second optical input beam is a THz frequency.

In a further aspect, the first optical input beam and the second optical input beam are both emitted from a single emitting device, and the emitting device may be a laser, and, more particularly, the emitting device is not a THz frequency emitting source.

According to still further aspects, the first optical input beam and the second optical input beam are emitted from differing emitting devices, and the emitting devices may be lasers, but neither optical input beam is emitted from a THz emitting source.

According to a further aspect, the output beam is non-co-linear with the first optical input beam and/or second optical input beam.

Still further, according to one aspect, the first optical input beam and the second optical input beam are directed onto the region of the substrate surface simultaneously or substantially simultaneously.

According to another aspect, the present disclosure is directed to a system for characterizing a substrate surface. The system comprises one or more one optical emitting devices for emitting a first optical input beam having a first frequency and a second optical input beam having a second frequency and a THz detector, wherein the one or more optical emitting devices is positioned to direct the first optical input beam and the second optical input beam to a region of the substrate surface, wherein the first frequency of the first optical input beam differs from the second frequency of the second optical input beam, and wherein the THz detector is positioned to receive a THz output beam formed from a mixing of the first optical input beam and the second optical input beam at or beneath the substrate surface. The THz detector is in communication with computer software and/or hardware configured to measure one or more properties of the substrate material surface based on the THz output beam received by the detector.

In a further aspect, the first optical input beam and the second optical input beam are both emitted from a single emitting device that is not a THz frequency emitting source. In another aspect, the single emitting device is a laser.

In a still further aspect, the system comprises a plurality of optical emitting devices and the first optical input beam and the second optical input beam are emitted from differing emitting devices, and wherein neither the first optical input beam nor the second optical input beam is emitted from a THz emitting source.

In a further aspect, the first optical input beam and the second optical input beam are each emitted from a laser.

In another aspect, the output beam is non-co-linear with the first optical input beam and/or second optical input beam.

In a still further aspect, the systems of the present disclosure further comprise computer software and/or hardware configured to measure one or more properties of the substrate surface based on the output beam received by the detector.

According to another aspect of the systems of present disclosure, one or more optical emitting devices comprises one or more controls selected from a group comprising an optical input beam frequency control, an optical input beam intensity control, an optical input beam bandwidth control, and combinations thereof.

In a further aspect, the systems of the present disclosure comprise emitting devices having one or more controls that produce a frequency difference between the first optical input beam and the second optical input beam that is a THz frequency.

Still further aspects are directed to apparatuses comprising a system for characterizing a substrate surface. The apparatuses comprise one or more one optical emitting devices for emitting a first optical input beam having a first frequency and a second optical input beam having a second frequency and a THz detector, wherein the one or more optical emitting devices is positioned to direct the first optical input beam and the second optical input beam to a region of the substrate surface, wherein the first frequency of the first optical input beam differs from the second frequency of the second optical input beam, and wherein the THz detector is positioned to receive a THz output beam formed from a mixing of the first optical input beam and the second optical input beam at or beneath the substrate surface.

In a still further aspect, the methods, systems and apparatuses of the present disclosure are directed to a vehicle comprising a substrate material surface, wherein at least a portion of the substrate material surface is interrogated by directing a first optical input beam from a first optical source having a first frequency onto a region of a substrate material surface. A second optical input beam from a second optical source having a second frequency is directed onto the region of the substrate material surface, with the first frequency of the first optical input beam differing from the second frequency of the second optical input beam. The first and second optical input beams are mixed at or beneath the substrate material surface to provide an output beam having a THz frequency. The output beam is directed to and received by a THz detector, and one or more properties of the substrate material surface are measured based on the output beam received by the detector.

In a further aspect the vehicle includes, but is not limited to, manned or unmanned objects and structures in an atmospheric or space environment. Contemplated objects include vehicles, such as, for example, aircraft, satellites, rockets, missiles, etc., and therefor include manned and unmanned aircraft, spacecraft, terrestrial vehicles, non-terrestrial vehicles and even surface and sub-surface water-borne marine vehicles, objects and structures.

For the purpose of this disclosure, the terms "area", "location" and "region" are used interchangeably and have equivalent meaning when referring to the substrate material.

For the purpose of this disclosure, the terms "beam" and "signal" may be used interchangeably and have equivalent meaning when referring to the substrate material.

For the purpose of this disclosure, the terms "interrogation" and "characterization" are used interchangeably and have equivalent meaning when referring to the substrate material.

The methods, systems and apparatuses of the present disclosure provide solutions to the problems of accurately and cost-effectively interrogating and evaluating substrate material surface and sub-surface characteristics including, but not limited to the interrogation and evaluation of chemical composition, homogeneity, heterogeneity, mechanical surface irregularities (including, but not limited to, defects and contamination), crystallographic defects, surface, etc., and combinations thereof.

BRIEF DESCRIPTION OF THE DRAWINGS

Figure 1:
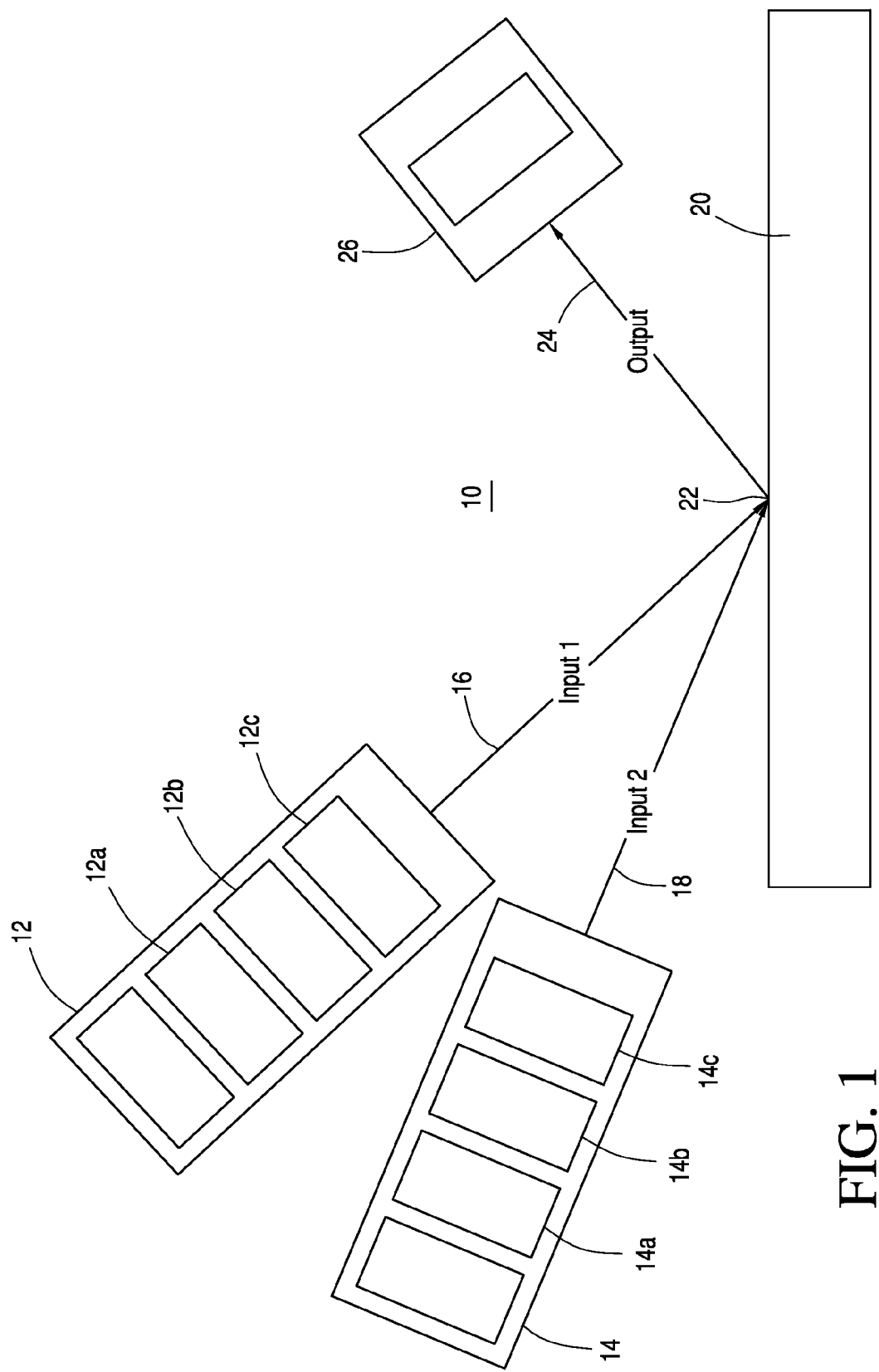
Figure 2:
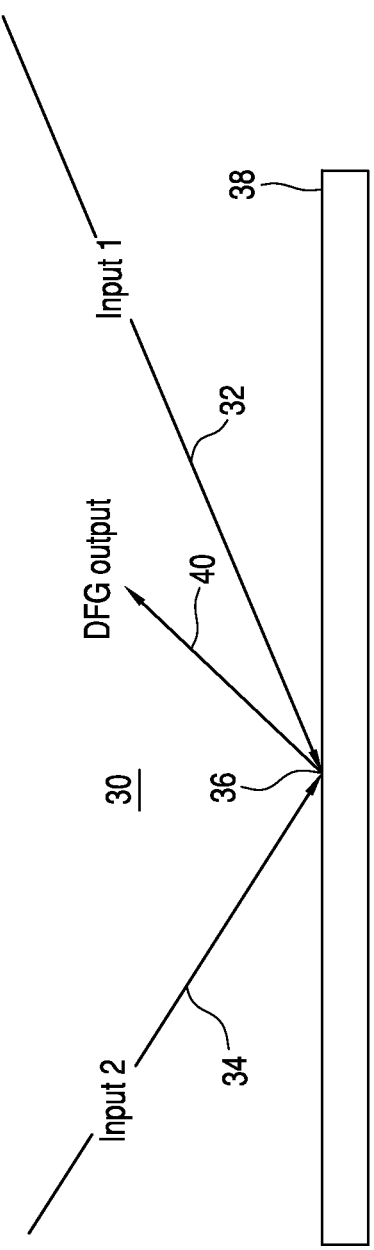
Figure 3:
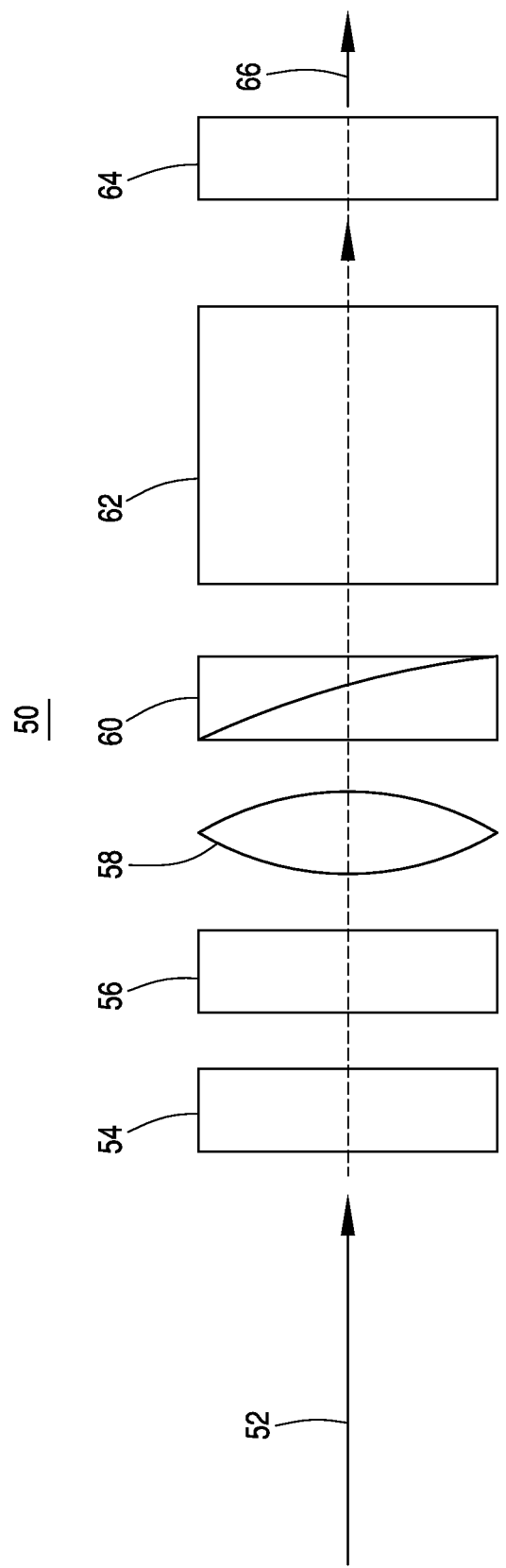
Figure 4:
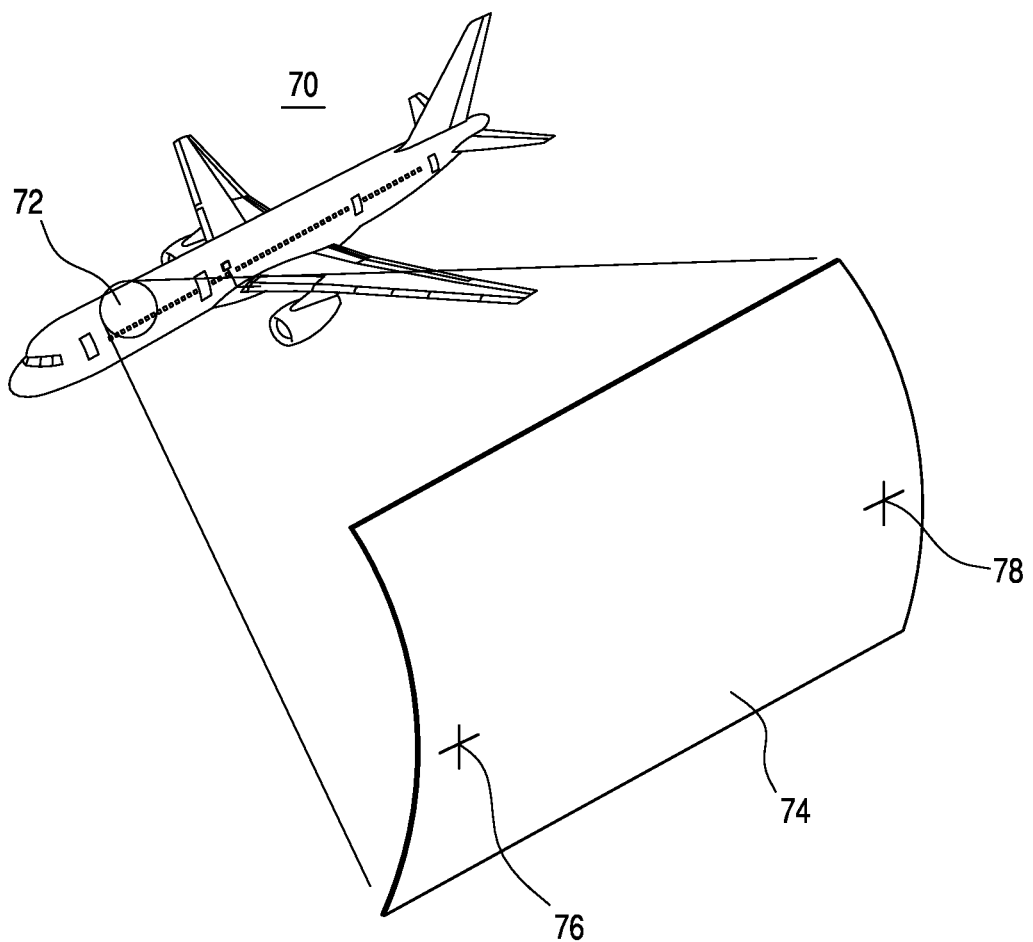

Having thus described variations of the disclosure in general terms, reference will now be made to the accompanying drawings, which are not necessarily drawn to scale, and wherein:

FIG. 1 is a schematic diagram of one aspect of the present disclosure;

FIG. 2 is a schematic diagram of a variation of the present disclosure;

FIG. 3 is a schematic diagram showing a variation of the present disclosure; and FIG. 4 is a drawing of an aircraft comprising material interrogated by an aspect of the present disclosure.

DETAILED DESCRIPTION

According to aspects of the present disclosure, THz spectroscopy can be used for material evaluation and characterization without the use of a THz input source. The required frequencies are obtained by providing difference frequency generation (DFG) at a material surface interface. It has now been determined that, so long as the difference between the input frequencies from the input sources are in the THz regime, a useful THz output will be generated at the material surface, and the THz output signal can be interrogated with an appropriately positioned THz sensor. In contrast to THz sources, the optical systems disclosed herein can be operated with reduced cost, reduced maintenance, and can be set up easily and inspected quickly and easily.

According to a further aspect, optical (laser) inputs may be used to achieve the desired input frequencies, and the inputs are tuned to differ in frequency by the THz frequency. In an alternate aspect, an individual laser contains multiple frequency components to achieve a THz frequency.

According to aspects of the disclosure, since there is a substantial shift achieved in frequencies between the input and output frequencies, the background signal is greatly reduced, thus producing higher signal to noise ratio and overcoming problems previously associated in the field.

Since difference frequency is a coherent process, the THz signals maintain their properties when analyzing (evaluating, characterizing, etc.) a surface. Such maintenance of THz signal properties is not intrinsically possible with known THz sources. According to one example, a laser can be used that has longitudinal line spacing substantially equal to the THz resonance in the material response at the substrate material surface being characterized. An operation laser's so-called longitudinal modes are defined by the spacing in the resonator mirrors. Specifically, only modes that have a half integral number of wavelengths will be supported in the cavity. This means that only those wavelengths or equivalent frequencies will be present in the output frequencies or bandwidth of the laser. The contemplated optical sources contemplated according to the present disclosure, will be those disclosed elsewhere herein. In other words, the use of solid state lasers as optical sources that can be operated in pulse mode with reasonably high peak intensities of from about 1 KW/cm$^2$ to about 1 GW/cm$^2$ is contemplated. As would be readily understood, the laser cavity of the first and second optical sources may be optimized, such that a spacing in the longitudinal modes of laser operation for each optical source will differ by a desired THz frequency.

In another aspect, the first input beam and the second input beam are directed onto a region of the substrate material simultaneously or substantially simultaneously. It is understood that pulsed lasers have a temporal duration of, typically about, one nanosecond or one picosecond. Therefore, according to this specification, the term "substantially simultaneously" refers to laser pulses arriving at a predetermined area on a substrate material surface, such that their pulses arrive at the substrate material surface in overlapping fashion, and the pulses are out of synch for a duration of only from about 50 to about 100 picoseconds.

The source responsible for the DFG is the nonlinear polarization P$^{(2)}$ in the medium.

$$\vec{P}^{(2)}(\omega_{THz}=\omega_1-\omega_2)=\vec{\chi}^{(2)}(\omega_{THz}):\vec{E}(\omega_1)\vec{E}(\omega_2). \quad (2)$$

If the medium has an inversion symmetry, then the non-linear susceptibility $\vec{\chi}^{(2)}$ vanishes in the electric-dipole approximation. Since the inversion symmetry is necessarily broken at an interface, this makes DFG an effective surface probe. For a monolayer of molecules at a surface, the surface non-linear susceptibility is typically ~$10^{-15}$ esu, which should yield a signal of $10^3$ photons/pulse with a laser pulse of 10 milliJoule energy and 10 nsec duration impinging on a surface area of 0.2 cm$^2$.

The resonant behavior of $\vec{\chi}^{(2)}$ can provide spectroscopic information about a surface or molecules adsorbed at the surface. However, if optical wavelengths are involved in the inputs, which are generally in the 0.2-1 micron (μm) range, only electronic transitions of the molecules or surface structure can be probed. Such wavelengths usually have relatively broad bandwidths, making DFG not particularly useful for identification or selective monitoring of surface molecular species. Vibrational spectroscopy is more suitable for selective studies of adsorbed molecules and their interaction with the substrate. Vibrational modes appear in the IR or THz range, and sources in the THz range suitable for nonlinear optics, do not exist.

In the DFG process, the difference in frequency between the two non-THz input beams is tuned through a vibrational resonance, and the THz signal is generated directly at the surface. When the difference frequency is resonant with a material resonance at the surface, $\bar{\bar{\chi}}^{(2)}$ has a resonant enhancement (i.e., it gets larger) so the THz response can be measured even though the inputs are in the optical regime.

FIG. 1 shows a schematic representation of one aspect of the present disclosure. Diagnostic system 10 shows a first optical source 12 and a second optical source 14. First optical source 12 comprises a first optical source frequency control 12a, a first optical source intensity control 12b and a first optical source bandwidth control 12c. Second optical source 14 comprises a second optical source frequency control 14a, a second optical source intensity control 14b, and a second optical source bandwidth control 14c. In one aspect, the frequency and bandwidth controls on the first and second optical sources are such that the frequency separation of the optical sources is equal or substantially equal to the THz frequency of interest. First optical source 12 emits a tunable non-THz range first input beam 16 that is directable onto a preselected location 22 on a surface 20 being interrogated. Second optical source 14 emits a tunable non-THz range second input beam 18 that is directable onto a preselected location 22 on a surface 20 being interrogated. The first and second optical sources are positioned and aligned in a predetermined orientation so that their surface areas of optical illumination overlap on the interrogated surface 20. This alignment may be implemented via a series of refractive and reflective elements. For example, by changing their tilt in two axes, elements in series can propagate a laser beam to any position on a surface. The non-THz range first and second input beams 16, 18 interact in a predetermined fashion at the predetermined location 22 on surface 20, such that a combined output signal 24 that is now in the terahertz range is directed away from the preselected location 22 on surface 20. The combined output signal from the first and second optical sources 12, 14 are in the terahertz range of from about 0.1 to about 10 THz. Terahertz detector 26 is positioned to receive the THz range output signal 24 from the predetermined location 22 on surface 20.

A THz detector typically comprises some manifestation of a bolometer, meaning that the detector detects the presence of THz radiation by assessing an increase in temperature caused by observing the THz radiation. In one contemplated variation, THz radiation is detected by up-converting the THz radiation into the infrared (IR) or optical regime, and detecting that radiation with detectors operating in that "up-converted" spectral range. Intensity controls can include broadband filters for reducing intensity, or certain frequency notch filters that are intended to drop intensity levels where the detectors can act in a linear fashion. Polarization control is typically done by including, for example, some combination of polarization sensitive optical media. This may include thin-film polarizers, or include more elaborate schemes such as, Glan-Thompson systems or Glan-air polarizer systems, etc. In addition, optics based on Brewster's angle may be used for polarization selectivity.

Frequency controls can be accomplished by frequency dependent color filters or dielectric filters. A more elaborate system can be achieved for frequency control by a combination of spectrophotometers typically comprising diffraction grating, such as, for example, those operating in a frequency or bandwidth of interest.

The first optical source 12 includes a visible input in optical communication with associated input optics. The first optical source preferably comprises a narrow frequency bandwidth visible pulse laser, such as, for example a pulsed diode laser, a continuous wave diode laser, a pulsed solid state laser, or a continuous wave solid state laser.

In another contemplated configuration, the optical sources are not necessarily lasers. In this contemplated variation, it is not required that the optical source inputs are coherent. While, using non-coherent optical source inputs present various challenges not present with the use of coherent optical source inputs, nothing in the present disclosure limits the use of coherent or non-coherent optical sources, except that the selected optical sources do not emit radiation in the THz regime.

The second optical source 14 includes a visible input in optical communication with associated input optics. The input is preferably a narrow frequency bandwidth laser including but not limited to a visible pulse laser, a pulsed diode laser, a continuous wave diode laser, a pulsed solid state laser, a continuous wave solid state laser, etc. According to one aspect, the second source will has characteristics similar to the first source, however, the peak frequency of the second source is separated from the peak frequency of the first source by a desired THz frequency. Because the diagnostic methods, systems and apparatuses of the present disclosure involve a non-linear interaction with a substrate material surface, pulse lasers with reasonable peak intensities of from about 1 KM/cm$^2$ to about 1 GW/cm$^2$ are preferred. Particularly useful lasers include, for example, but are not limited to, solid-state lasers such as Nd:YAG lasers, Ti:sapphire lasers, etc. Such lasers are commercially available. As stated above, while the choice of the first optical source is arbitrary, the second optical source must have a center operating frequency that differs from the first optical source frequency by a THz frequency being examined.

The frequency structure of the laser pulse may comprise several frequencies, with the lines defined by the longitudinal modes of the laser. As an alternative to narrowing the bandwidth, the longitudinal modes of each input can be spaced so that the difference frequency between the modes will form the THz frequency difference. This will allow for the DFG process to occur, even if the overall bandwidths of the laser pulses are broad. According to another variation, a single laser may be used having individual longitudinal lines to form the DFG inputs. A THz signal is then be created by the DFG between those individual lines.

Because the THz frequency is considerably smaller than the frequencies of the first and second optical inputs, care must be given to control the frequency characteristics of the inputs. For example, the bandwidths of the optical inputs must be narrow as compared to the desired frequency difference of the inputs. If the bandwidths are not sufficiently narrow, the frequency signal will be obscured by the bandwidths of the individual optical source inputs. The frequency bandwidth of the lasers must be narrow compared to the separation that is desired. For example, if the desired difference is 10 THz, the bandwidth of each optical source must be narrow, compared to the desired difference frequency. The precise frequency bandwidth depends upon the particular application. Generally, the bandwidth should be no greater than one-third of the separation. According to one aspect of the disclosure, the bandwidth should be a factor of 10 or more, smaller than the separation. The bandwidth can be controlled by careful construction of the optical source, since mechanical stability and thermal stability translate into narrow bandwidth. For example, external cavity solid-state lasers exist commercially that operate at THz bandwidth that is much narrow than what is required by contemplated aspects of the present disclosure. In addition, the use of the native cavity frequency-selective element, such as a diffraction grating, will allow the second optical source to be frequency-tuned to a value that is separated from the first optical source frequency value in terms of THz frequency.

FIG. 3 shows a schematic diagram of the THz components present in the THz detector 26 according to one variation. According to system array 50 shown in FIG. 3, the DFG signal 52 is directed to and received by a direction selector 54, such as, for example, an iris. DFG signal 52 then proceed through direction selection 54 and through the following components in sequence: broadband frequency selector 56; collection device, such as, for example, a lens or lens combination 58; a polarization selector 60 to accept p or s as needed; a spectrophotometer 62; and electrical signal converter 64, such as, for example, a photodiode or equivalent component for use to convert a signal in the visible spectrum. A converted electrical signal 66 then passes from the system array 50 to processing architecture (not shown) in communication with desired computer hardware and software that is able to recognize, interpret, classify and otherwise assist in the interrogation of the substrate material.

According to an aspect of the disclosure, the detector 26 comprises components necessary to receive and process the signals generated by the combined first and second inputs that are reflected from a substrate surface being interrogated and then sent as output to the detector. According to one contemplated variation, within the detector 26, signal collection optics receive the combined output from the first and second optical sources that is reflected from the surface being interrogated. According to another aspect of the present disclosure, the detector 26 is responsive at the THz frequency band and comprises, at least, a frequency (wavelength) THz discriminator, an intensity control, and a polarization discriminator.

According to further aspects of the disclosure, detection apparatuses will comprise frequency-selective elements to allow discrimination between the difference frequency signal and other ambient or interfering signals that may be generated in the area of measurement at or beneath the substrate material surface. The signal collection optics direct the propagation of the output from the first and second optical sources so that a collected optical light signal is formed after propagation through the signal collection optics. The signal collection optics may be either refractive or reflective optics that act to control the divergence of the light coming from the surface being interrogated so that as much of the light signal as possible is collected for analysis. According to a further variation, an optical detector converts the collected optical light signal to an electronic signal, thus monitoring the intensity of the DFG as a function of surface characterization. An electronic signal analyzer analyzes the electron signal for providing surface-sensitive spectroscopic characterizations. According to one aspect, the electronic signal analyzer may comprise, for example, a computer with suitable internal electronics, including appropriate hardware and software, to implement the appropriate mathematical algorithms to interpret the received electronic signals. According to one aspect, the presence of contamination on a surface being interrogated will change the spectroscopic response of the surface. Since the amount of light generated at the DFG wavelength will depend upon the surface spectroscopy, appropriate interpretation of the electronic signal provides a means to monitor the amount of contamination present on the surface.

According to one aspect, because the optical sources of the present disclosure require diagnostics requiring a non-linear optical source interaction, pulse lasers with desired peak intensities of from about 1 KW/cm$^2$ to about 1 GW/cm$^2$ are contemplated. One contemplated laser source are solid-state lasers, such as, for example, Nd:YAG lasers operating on the 1.064 micron line, or a Nd:YAG laser and a harmonic converter for operation at the second or third harmonic of the fundamental output wavelength. Such a source may operate with a maximum pulse length of about 10 nsec, with the optimal pulse length being about 10 psec. The useful range for the difference frequency is the THz spectrum of from about 0.1 THz to about 100 THz. More complex lasers such as Ti:sapphire lasers are also contemplated. The contemplated lasers are commercially available from sources including Coherent, Spectra-Physics, Melles-Griot, etc.

According to further aspects, the optical sources comprise tunable visible input capabilities including steering apparatuses that may comprise mirrors aligned so that their surface normal are non-coplanar, with the mirrors' reflectances being optimized for an output wavelength of the tunable visible laser. Polarizers may be used that are operative in the visible range so that an output wavelength is p or s polarized with the polarization referenced to the surface to be interrogated. In one aspect, a spot shaping apparatus is used that may include a series of lenses for creating a predetermined and controlled spot size on the surface to be interrogated. The lenses may be transparent in the visible range.

The output wavelength discriminator preferably includes an iris, a filter in communication with the iris for passing the DFG wavelength, and a polarizer in optical communication with the filter aligned to detect either the p or s polarization and referenced to the surface where the DFG light is generated.

According to another aspect of the disclosure, the signal collection optics may include a telescope system comprising a plurality of lenses having desired materials and coatings optimized for the DFG wavelength, in the wavelength band from about 0.3 mm to about 30 microns. The optical detector may be based on a semiconductor material such as, for example, silicon, germanium, etc. depending upon the precise wavelength to be detected. The detector may be electronically gated to only detect output light generated by the input laser pulses. A computer collects and analyses the electronic data from the optical detector.

According to aspects of the present disclosure surface and sub-surface substrate material inspection is accomplished by the methods, systems and apparatuses presented herein. Such sub-surface inspection is accomplished by effecting a predetermined penetration of the radiation from the optical source inputs to a predetermined depth beneath the substrate material surface. According to aspects of the disclosure, penetration is effected on the order of the wavelength of the substrate material being interrogated. Since the THz wavelength is on the order of 1 mm, a penetration depth approximately equal to at least about 1 mm is achieved. If the material substrate material being interrogated is transparent (not opaque) or translucent at the THz frequencies, the penetration depth will be deeper, extending to a sub-surface depth of several millimeters. In this way sub-surface defects that are not otherwise detectable with visible or infrared inspection techniques are detectable according to the methods, systems and apparatuses of presented herein.

A further aspect is illustrated in FIG. 2. FIG. 2 shows an alternate positioning of the optical sources as compared to their orientation as shown in FIG. 1. As shown in FIG. 2, diagnostic system 30 shows a first optical source input 32 from a first optical source (not shown) and a second optical source input 34 from a second optical source (not shown). As in diagnostic system 10 shown in FIG. 1, the first optical source of diagnostic system 30 comprises a first optical source frequency control, a first optical source intensity control, and a first optical source bandwidth control (all not shown). Second optical source of diagnostic system 30 comprises a second optical source frequency control, a second optical source intensity control, and a second optical source bandwidth control (all not shown). In one aspect, the frequency and bandwidth controls on the first and second optical sources are such that the frequency separation of the optical sources is equal or substantially equal to the THz frequency of interest. First optical source input 32 is a tunable non-THz range input beam that is directable onto a preselected location 36 on a surface 38 being interrogated. Second optical source input 34 is a tunable non-THz range input beam that is directable onto a preselected location 36 on a surface 38 being interrogated. The first and second optical sources are positioned and aligned in a predetermined orientation so that their surface areas of optical illumination overlap on the interrogated surface 38. This alignment may be implemented via a series of refractive and reflective elements. For example, by changing their tilt in two axes, elements in series can propagate a laser beam to any position on a surface. The non-THz range first and second input beams 32, 34 interact in a predetermined fashion at the predetermined location 36 on surface 38, such that a combined output signal 40 that is now in the THz range is directed away from the preselected location 36 on surface 38. The combined output signal from the first and second optical sources are in the THz range of from about 0.1 to about 10 THz. A THz detector (not shown) is positioned to receive the THz range output signal 40 from the predetermined location 36 on surface 40.

Although the aspects of the present disclosure are useful for all materials regardless of the materials' end uses, material and material surfaces interrogated by the methods, systems and apparatuses of the present disclosure are thought to be particularly useful interrogating materials used a components and parts in the manufacture of, for example, manned or unmanned objects and structures in an atmospheric or space environment. Contemplated objects include structures and vehicles, such as, for example, aircraft, satellites, rockets, missiles, etc., and therefor include manned and unmanned aircraft, spacecraft, terrestrial vehicles, non-terrestrial vehicles and even surface and sub-surface waterborne marine vehicles, objects and structures.

FIG. 4 is a drawing of a vehicle, and, in particular, an aircraft 70. Fuselage panel 74 having a substrate material surface is shown, in an enlarged configuration, as being located at the region of the fuselage at location 72. The marks shown as "+" 76, 78 represent locations on the substrate material surface of fuselage panel 74 that may be interrogated according to methods, systems and apparatuses of the present disclosure. While the drawing shows an aircraft with a portion of fuselage identified, it is understood that the methods, systems and apparatuses of the present disclosure contemplate use with any material substrate surface of any material that can be used anywhere in the construction of any vehicle, such as, for example an aircraft, including the interior, exterior or locations there between.

While the preferred variations and alternatives of the present disclosure have been illustrated and described, it will be appreciated that various changes and substitutions can be made therein without departing from the spirit and scope of the disclosure. Accordingly, the scope of the disclosure should only be limited by the accompanying claims and equivalents thereof.

We claim:

1. A method for evaluating a substrate material surface comprising:
   directing a first optical input beam from a first optical source having a first frequency onto a region of a substrate material surface;
   directing a second optical input beam from a second optical source having a second frequency onto the region of the substrate material surface, with the first frequency of the first optical input beam differing from the second frequency of the second optical input beam;
   mixing the first optical input beam and the second optical input beam reflected from the substrate material surface to provide an output beam having a Terahertz frequency;
   receiving the output beam with a Terahertz detector; and
   measuring one or more properties of the substrate material surface based on the output beam received by the detector.

2. The method of claim 1, wherein the difference between the first frequency of the first optical input beam and the second frequency of the second optical input beam is a Terahertz frequency of from about 0.1 to about 100 THz.

3. The method of claim 1, wherein the first optical input beam and the second optical input beam are both emitted from a single emitting device.

4. The method of claim 3, wherein the single emitting device is a laser.

5. The method of claim 3, wherein the single emitting device is not a Terahertz emission source.

6. The method of claim 1, wherein the first optical input beam and the second optical input beam are emitted from differing emitting devices.

7. The method of claim 6, wherein the first optical input beam and the second optical input beam are each emitted from a laser.

8. The method of claim 6, wherein neither the first optical input beam nor the second optical input beam is emitted from a Terahertz emitting source.

9. The method of claim 1, wherein the output beam is non-co-linear with the first optical input beam and/or second optical input beam.

10. The method of claim 1, wherein the first optical input beam and the second optical input beam are directed onto the region of the substrate material surface simultaneously or substantially simultaneously.

11. A system for characterizing a substrate material surface comprising:
   one or more one optical emitting devices for emitting a first optical input beam having a first frequency and a second optical input beam having a second frequency, said optical emitting devices positioned to direct the first optical input beam and the second optical input beam to a region of the substrate material surface, and the first frequency of the first optical input beam differs from the second frequency of the second optical input beam; and a Terahertz detector positioned to receive a reflected Terahertz output beam formed from a mixing of the first optical input beam and the second optical input beam reflected from the substrate material surface, said Terahertz detector comprising processing architecture in communication with computer software and/or hardware configured to measure one or more properties of the substrate surface based on the reflected Terahertz output beam received by the detector.

12. The system of claim 11, wherein the first optical input beam and the second optical input beam are both emitted from a single emitting device that is not a Terahertz emission source.

13. The system of claim 12, wherein the single emitting device is a laser.

14. The system of claim 11, wherein the system comprises a plurality of optical emitting devices and the first optical input beam and the second optical input beam are emitted from differing emitting devices, and wherein neither the first optical input beam nor the second optical input beam is emitted from a Terahertz emission source.

15. The system of claim 14, wherein the first optical input beam and the second optical input beam are each emitted from a laser.

16. The system of claim 11, wherein the Terahertz detector further comprises processing architecture comprising computer software and/or hardware configured to measure one or more properties of the substrate surface based on the output beam received by the detector.

17. The system of claim 11, wherein the one or more optical emitting devices comprise one or more controls selected from the group consisting of: an optical input beam frequency control, an optical input beam intensity control, an optical input beam bandwidth control, and combinations thereof.

18. The system of claim 17, wherein the one or more controls produces a frequency difference between the first optical input beam and the second optical input beam that is a Terahertz frequency.

* * * * *